United States Patent [19]

Revici

[11] Patent Number: 5,153,221
[45] Date of Patent: Oct. 6, 1992

[54] METHOD FOR THE TREATMENT OF ACQUIRED IMMUNE DEFICIENCY SYNDROME

[75] Inventor: Emanuel Revici, New York, N.Y.
[73] Assignee: Elena Avram, New York, N.Y.
[21] Appl. No.: 593,032
[22] Filed: Oct. 5, 1990
[51] Int. Cl.$^5$ .................. A61K 31/19; A61K 31/20
[52] U.S. Cl. .................................. 514/557; 514/558
[58] Field of Search ............................... 524/557, 558
[56] References Cited

U.S. PATENT DOCUMENTS 4,681,753  7/1987  Revici .................................. 424/10

Primary Examiner—Jerome D. Goldberg
Attorney, Agent, or Firm—McAulay Fisher Nissen Goldberg & Kiel

[57] ABSTRACT

A method and composition for the treatment of a patient with AIDS. The composition comprises an AIDS-symptom alleviating effective amount of an aliphatic carboxylic acid having an odd number of carbon atoms and containing at least 5 and not more than 10 carbon atoms. The composition may be administered in a pharmaceutically acceptable oily carrier and is administered orally and/or by intramuscular injection.

9 Claims, No Drawings

METHOD FOR THE TREATMENT OF ACQUIRED IMMUNE DEFICIENCY SYNDROME

BACKGROUND OF THE INVENTION

The study of the pathogenic factors of diseases caused by the HIV virus, e.g., the acquired immune deficiency syndrome (AIDS), has shown that, in addition to the presence of the virus, parasitated lymphocytes which have been infected by the virus are present which represent the detectable lesions of the of the disease. Accordingly, in a therapeutic approach to this disease, an attempt to destroy the parasitated lymphocytes must be considered, in addition to treatment having a direct antiviral action.

Studies of the parasitated or infected lymphocytes has shown that they, like other lesions in the body, contain free lipids. They are especially sensitive to the action of agents having a lipidic character when introduced into the body.

SUMMARY OF THE INVENTION

I have discovered that certain lipidic agents have a specific capacity to act upon the pathogenic factor of AIDS. These agents act upon the virus itself, as well as the infected or parasitated lymphocytes. In particular, I have discovered that aliphatic organic compounds having five or more carbons and a lipidic character, i.e., are soluble in unpolarized or organic solvents rather than water, provide an effective procedure for the treatment of AIDS. These compounds appear to be bound by the viruses and the parasitated lymphocytes through the free lipids of the virus and lymphocytes.

More specifically, I have found that compounds having a negative polar group and, especially, an acidic polar group, exhibit a characteristic antiviral activity and effect in decreasing the number of parasitated lymphocytes.

The method of the invention comprises administering to a patient with AIDS, an anti-AIDS symptom reducing effective amount of an organic aliphatic acid having at least 5 carbon atoms and an odd number of carbon atoms.

DETAILED DESCRIPTION OF THE INVENTION

Organic acids particularly suitable for use with the present invention are pentanoic, nonanoic and heptanoic acid. Most preferred is heptanoic acid. Each of these compounds exhibit not only anti-HIV virus effects, but also affect the parasitated or infected lymphocytes, killing them.

The compounds are administered intramuscularly or orally from oily solutions. Conventional organic oils which are pharmaceutically acceptable may be used as the oily carrier. Typically, for example, vegetable oils, and most preferably, polyunsaturated oil, such as, safflower oil, are suitable. For oral administration, a solution having a concentration from about 20 to 60%, and preferably, about 50% and in amounts of from about 1 to 5 ml per dosage, two to four times a day, are effective. For intramuscular injection, oily solutions having concentrations up to 30% acid may be used with injection volumes being from about 2 to 10 ml per injection, one to four times per day. (All concentrations are expressed as volume/volume percent.) I have found that these administrations are well tolerated. The inventive method may be utilized with oral or intramuscular injection alone or in combination. The administration of the medicament may be continued for as long as necessary.

Toxicity studies with these acids have shown that they are essentially non-toxic in mice after repeated injections of 0.5 ml of a 10% volume/volume solution for more than two months. No toxic effects were observed in rats with daily injections of 1 ml of a 10% volume/volume solution.

In addition, for all of the patients described hereinafter, no complaints of any side effects were received, even when relatively large amounts of medication were administered.

A group of forty AIDS patients was treated utilizing heptanoic acid. The patients were diagnosed as having AIDS by conventional analysis. These patients were each treated orally with heptanoic acid in safflower oil, in 50% oily solution, in doses from 2–5 ml, two to four times a day for more than one month. Impressive subjective changes and improvements in the condition of each of the patients were seen, even beginning after the first administration. No toxic effects after prolonged treatment with higher amounts were observed.

Ten patients diagnosed with AIDS and having chronic diarrhea were treated. These patients had chronic diarrhea for more than month which did not respond to any conventional treatment. They received from 2–5 ml of the 50% heptanoic acid orally in safflower oil, three to four times a day. Using this inventive method, this symptom was fully controlled within a period of less than one week in each of these patients.

This treatment has also produced significant changes in the ratio of helper to suppressor lymphocytes. Generally, the normal ratio of helper to suppressor lymphocytes should be about 1.2. With patients having AIDS, this ratio is as low as 0.1. With the inventive treatment, improvements in increasing this ratio are seen beginning with the initial treatment and continuous improvement has been seen after treatments for a period of one month.

The following are details of two of the forty clinical treatments referred to above.

J. D., 38 years old, with a $T_4/T_8$ ratio of 0.14, exhibited severe manifestations of AIDS, including diarrhea and fever. Within one week of treatment with 3 ml of a 50% volume/volume heptanoic acid in safflower oil, these symptoms were fully controlled. After a two-month treatment of 2 ml of this medication three times a day orally, he remained symptom free for six months without any further treatment. His $T_4/R_8$ ratio remained at a level of about 1.0.

L. S., 24 years old, diagnosed with AIDS. He was rapidly deteriorating for the month prior to his beginning treatment. The manifested symptoms were primarily fatigue, loss of weight, loss of appetite, fever and multiple lymphatic gland involvement. The $T_4/T_8$ ratio was 0.2. Within one week of treatment with 3 ml of 50% volume/volume heptanoic acid in safflower oil, orally four times a day, these symptoms were controlled.

After two months of treatment, the patient has remained in exceptional good clinical condition for the last six months, continuing with the treatment of 1 ml administered once a day. His $T_4/T_8$ ratio remain above 1.0.

In another variant of the present invention, a mixture of 30% heptanoic acid, 15% pentanoic acid, and 15% nonanoic acid (volume/volume percentage) in safflower oil were used orally with from 1 to 3 ml dosages four times a day. Clinical results in 12 patients with varying pathological AIDS manifestations all resulted in substantial improvements of their symptoms.

What is claimed is:

1. A method for the treatment of a patient with AIDS comprising administering to the patient orally or by intramuscular injection an AIDS-symptom alleviating effective amount of an aliphatic carboxylic acid having an odd number of carbon atoms and containing at least 5 and no more than 10 carbon atoms.

2. The method of claim 1 wherein the acid is selected from the group consisting of pentanoic acid, nonoic acid and heptanoic acid.

3. The method of claim 1 wherein the acid is heptanoic acid.

4. The method of claim 1 wherein the acid is dissolved in a pharmaceutically acceptable oil and the oil solution is administered to the patient.

5. The method of claim 4 wherein the oil is selected from the group of consisting of tung oil and safflower oil.

6. The method of claim 4 wherein the acid is administered orally in amount of from about 1 to 5 ml per dosage, two to four times a day.

7. The method of claim 6 wherein the concentration of the acid is from about 10 to 60 percent by volume.

8. The method of claim 4 wherein the acid is injected intramuscularly two to four times per day, the volume of each injection being from about 2 to 10 ml and the concentration of the solution being in the range from 10 to 30 percent by volume.

9. A method for the treatment of a patient with AIDS comprising administering to the patient both orally and by intramuscular injection an AIDS-symptom alleviating effective amount of an aliphatic carboxylic acid having an odd number of carbon atoms and containing at least 5 and no more than 10 carbon atoms.

* * * * *